US00PP17090P2

(12) United States Plant Patent
Yates

(10) Patent No.: US PP17,090 P2
(45) Date of Patent: Sep. 12, 2006

(54) ***JAMESBRITTENIA* PLANT NAMED 'YASAL'**

(50) Latin Name: *Jamesbrittenia hybrida*
Varietal Denomination: YASAL

(76) Inventor: Frederic Yates, The Orchard, Holmes Chapel Rd, Somerford, Congleton, Cheshire CW12 45P (GB)

( * ) Notice: Subject to any disclaimer, the term of this patent is extended or adjusted under 35 U.S.C. 154(b) by 0 days.

(21) Appl. No.: 10/883,836

(22) Filed: Jul. 6, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,574 P2 * 4/2002 Yates ..... Plt./263
PP12,576 P2 * 4/2002 Yates ..... Plt./263

OTHER PUBLICATIONS http://www.macore.com/index.htm Macore Labels Cards & Posters.* http://www.macore.com/gu/rp200305.htm Recent Photos & Updates.* http:www.macore.com/gu/58971717.htm Penny Candy (TM) Salmon Bacopa ppaf.*

UPOV ROM GTITM Computer Database, GTI Jouve Retrieval Software Jan. 2005/01 Citation for 'YASAL'.*

* cited by examiner

*Primary Examiner*—Kent Bell
*Assistant Examiner*—W. C. Haas

(57) ABSTRACT

A new cultivar of *Jamesbrittenia* plant named 'YASAL' that is characterized by salmon-pink flowers, bushy habit, and fragrant green leaves. In combination these traits set 'YASAL' apart from all others existing varieties of *Jamesbrittenia* known to the inventor.

2 Drawing Sheets

Botanical designation: *Jamesbrittenia hybrida.*
Variety denomination: 'YASAL'.

BACKGROUND OF THE INVENTION

The present invention relates to a new and distinct cultivar known botanically as *Jamesbrittenia* and referred to hereinafter by the cultivar name 'YASAL'. The genus *Jamesbrittenia* has been split from the genus *Sutera* under which plants of *Jamesbrittenia* have hitherto been classified.

'YASAL' was selected by the inventor in 2000 from a formal breeding program conducted in a cultivated area of Congleton, Cheshire, England and aimed at producing new varieties of *Jamesbrittenia* that exhibit improved habit and new flower colors. The breeding program was established by the inventor in 1994.

'YASAL' is an induced hybrid which resulted from and was selected as a single plant from the cross-pollination of female and male parent seedlings. The female parent is derived from cross pollinated unidentified *Jamesbrittenia* sp. hybrids (unpatented) and the male parent is derived from cross pollinated unidentified *Jamesbrittenia* sp. hybrids (unpatented) none of which have been released. Within the parentage are exhibited both mound forming and upright habits. 'YASAL' is distinguishable from the parent plants by salmon-pink flower color and bushy growth habit.

'YASAL' exhibits a bushy habit and salmon-pink flowers that distinguish it from all other *Jamesbrittenia* known to the inventor. The closest comparison plants are *Jamesbrittenia* 'Yagepin' (U.S. Plant Pat. No. 12,576) that exhibits pink flowers and *Jamesbrittenia* 'Yagero' (U.S. Plant Pat. No. 12,574) that exhibits rose-colored flowers. 'YASAL' is unique and distinguishable from the comparison plants by salmon-pink flower color.

The first asexual propagation of 'YASAL' was conducted in June of 2000 by the inventor in Congleton, Cheshire, England. The method of propagation used was softwood cuttings. Since that time the unique characteristics of 'YASAL' have been found stable in successive generations.

SUMMARY OF THE INVENTION

The following traits have been repeatedly observed and represent the characteristics of the new *Jamesbrittenia* cultivar 'YASAL'. These traits in combination distinguish this cultivar from all other commercial varieties known to the inventor. 'YASAL' has not been tested under all possible conditions and phenotypic differences may be observed with variations in environmental, climatic, and cultural conditions.

1. *Jamesbrittenia* 'YASAL' exhibits a bushy habit.
2. *Jamesbrittenia* 'YASAL' exhibits salmon-pink flowers.
3. *Jamesbrittenia* 'YASAL' exhibits fragrant green leaves.
4. *Jamesbrittenia* 'YASAL' is a perennial.
5. *Jamesbrittenia* 'YASAL' is propagated with softwood cuttings.
6. *Jamesbrittenia* 'YASAL' is 30 cm. in height and 50 cm. in width at maturity.
7. *Jamesbrittenia* 'YASAL' is suitable for use as a patio plant or hanging basket.
8. *Jamesbrittenia* 'YASAL' is hardy to USDA Zone 9.

BRIEF DESCRIPTION OF THE DRAWINGS

The accompanying color photographs illustrate the overall appearance of the new cultivar 'YASAL' showing the colors to be as true as is reasonably possible to obtain in colored reproductions of this type. The drawings were made in Arroyo Grande, Calif. of 9-month-old plants in 1-liter containers. Colors in the drawings may differ from the color values cited in the detailed botanical description, which accurately describe the actual colors of the new variety 'YASAL'.

The drawing labeled as FIG. 1 illustrates the plant from a side perspective.

Figure 1:
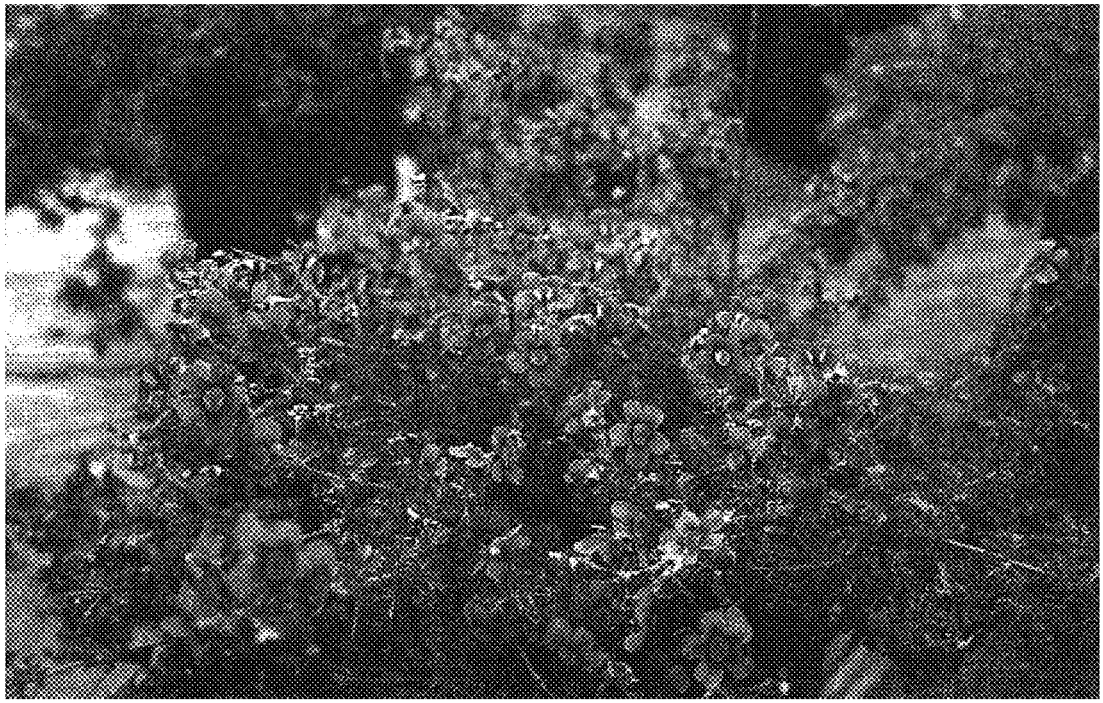
Figure 2:
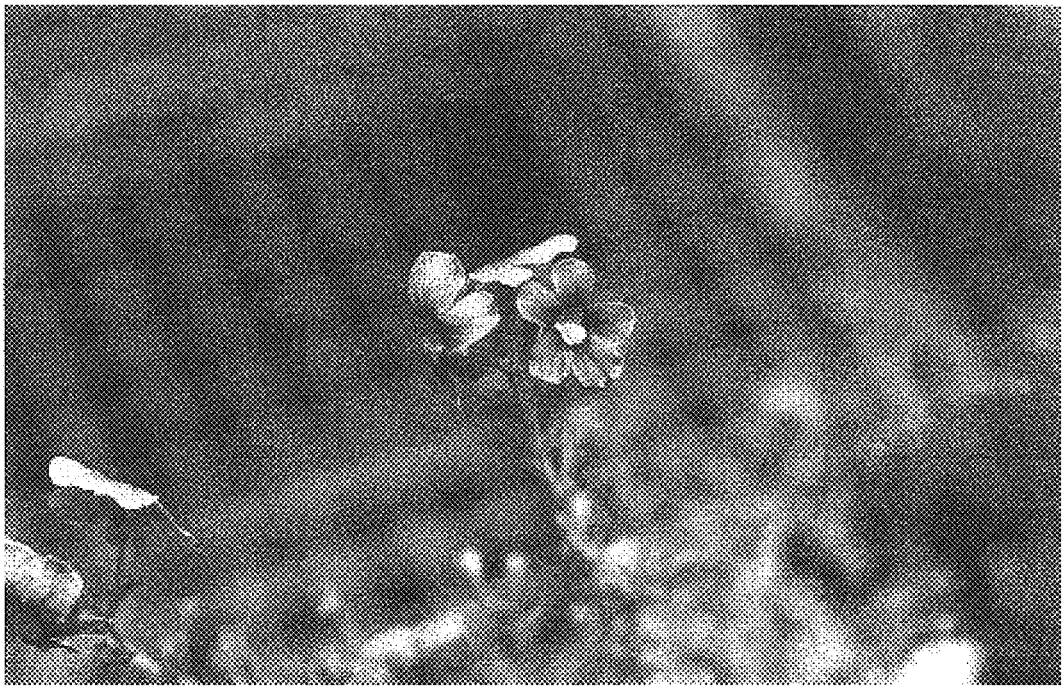

The drawing labeled as FIG. 2 illustrates a close-up view of the flower. The drawings were made using conventional photographic techniques and although foliage color may appear different from actual colors due to light reflectance, they are as accurate as possible by conventional photography.

BOTANICAL DESCRIPTION OF THE PLANT

The following is a detailed description of the new cultivar 'YASAL' as grown in a 1-liter container under unheated and well-ventilated greenhouse conditions in Encinitas, coastal California. Night minimum temperatures in such conditions are typically around 50 degrees Fahrenheit; day temperatures rarely exceed 75 degrees Fahrenheit. 'YASAL' received a standard commercial regime or irrigation and fertilization. Data was collected from 9-month-old plants. Phenotypic differences may be observed with variations in environmental, climatic, and cultural conditions. The color determinations are in accordance with the 2001 Edition of The Royal Horticultural Society Colour chart, except where general color terms of ordinary dictionary significance are used. There are no special growing requirements or growing problems known to the inventor.

Botanical classification: *Jamesbrittenia hybrida* 'YASAL'.
Common name: Bacopa or purple glory plant.
Use: Hanging basket or patio plant.
Parentage: 'YASAL' is a hybrid plant that resulted from the induced cross-pollination of the female and male parents plants. The male and female parents are unidentified *Jamesbrittenia* hybrids used in the inventors breeding program.
- *Female parent plant.*—Unidentified *Jamesbrittenia* sp. hybrid.
- *Male parent plant.*—Unidentified *Jamesbrittenia* sp. hybrid.

Propagation: Softwood cuttings.
Vigor: Vigorous.
Type: Perennial.
Plant dimensions: 18 cm. in height and 32 cm. in width in a one-liter container.
Quantity of flowers: 24 flowers on a one-liter container.
Quantity of buds: 25 buds on a one-liter container.
Fertility: Self-sterile.
Root system: Fine, branching.
Plant habit: Bushy.
Cropping time: 12 weeks are needed to produce a finished 4-inch commercial container.
Time to develop roots: 10 days are needed to develop roots on an initial cutting.
Temperature to develop roots: 17–22° Centigrade.
Seasonal interest: Flowers bloom in winter, spring and summer.
Hardiness: USDA Zone 9.
Sunlight requirements: Grows well and produces typical flower color in conditions of full sun if day maximum temperatures remain at or below 80 degrees Fahrenheit. In higher temperature conditions, partial shade is recommended
Soil requirements: Free-draining nursery compost or peat.
Diseases: 'YASAL' is susceptible to infections of downy mildew if grown in conditions of high humidity, that is, above 85% relative humidity, especially if exacerbated by limited airflow caused by growing plants with inadequate spacing. The particular species of downy mildew known as *Peronospera* sp has been identified on 'YASAL'. Infections of downy mildew may be averted or controlled by routine and rotating applications of different commercial fungicides registered for mildew control in order to minimize the risk of mutated resistant strains.
- *Pests.*—'YASAL' has not been observed to be notably susceptible or resistant to any particular pests of greenhouse ornamentals.

Stem:
- *Stem shape.*—Cylindrical.
- *Stem color.*—144A.
- *Stem demensions.*—7–18 cm in length by 2 mm in diameter.
- *Internode length.*—1.5–2 cm between nodes.
- *Stem surface.*—Stipitate glandular.
- *Branching habit.*—Basal branching.
- *Fragrance.*—Resinous turpentine-like scent.

Foliage:
- *Leaf arrangement.*—Predominately alternate, with a few opposite.
- *Leaf division.*—Simple.
- *Shape.*—Ovate.
- *Base.*—Attenuate.
- *Apex.*—Acute.
- *Venation pattern.*—Palmate.
- *Vein color* (*abaxial and adxial surfaces*). —138C.
- *Margins.*—Incised.
- *Leaf surface* (*abaxial and adaxial*).—Stipitate glandular.
- *Leaf color* (*adaxial surface*).—138A.
- *Leaf color* (*abaxial surface*).—138B.
- *Leaf dimensions* (*mature leaves*).—8 mm. in length and 5 mm. in width.
- *Leaf dimensions* (*young leaves*).—1.50 cm. in length and 1.25 cm. in width.
- *Leaf fragrance.*—Resinous turpentine-like scent.
- *Attachment.*—Petiolate.
- *Petiole dimensions* (*mature and young leaves*).—5 mm. in length and 1 mm. in width.
- *Petiole shape.*—Sulcate.
- *Petiole surface.*—Stipitate glandular.
- *Petiole color.*—137C.

Flower:
- *Inflorescence.*—Single flower.
- *Aspect.*—Outward and upward.
- *Flower shape.*—Circular, petals explanate.
- *Flower dimensions.*—2.25 cm. in diameter and 0.75 cm. in depth.
- *Flower color.*—185D, 186A and 23B are all present on an individual flower.
- *Bud shape.*—Globular.
- *Bud color.*—23C.
- *Bud dimensions.*—2 mm. in length and 2 mm. in width.
- *Bud surface.*—Pubescent.

*Number of petals.*—Five in number.
*Petal shape.*—Rotund.
*Petal apex.*—Obtuse to emarginated.
*Petal base.*—Cuneate.
*Petal dimensions.*—12 mm. in length and 7–8 mm in width.
*Petal surfaces* (*adaxial and abaxial surfaces*).—Glabrous.
*Petal margins.*—Entire and slightly ruffled.
*Petal color* (*adaxial surface*).—23B, 185D and 186A are all individually present on an individual petal.
*Petal color* (*abaxial surface*).—186C and 186B are both individually present on an indivdual petal.
*Corolla tube color* (*inside surface*).—23B.
*Corolla tube color* (*outer surface*).—23C.
*Corolla tube depth.*—6 mm. in depth.
*Peduncle color.*—143C.
*Peduncle dimensions.*—3.5 cm. in length and 1 mm. in width.
*Peduncle shape.*—Cylindrical.
*Peduncle surface.*—Stipitate glandular.
*Flowering season.*—Spring and summer.
*Flowering time.*—Diurnal.
*Calyx color.*—138A.
*Calyx shape.*—Bell-shaped.
*Calyx surface.*—Pubescent.
*Number of sepals.*—Five sepals in number.
*Sepal color* (*adaxial and abaxial surfaces*).—138A.
*Sepal surface.*—Stipitate glandular.
*Sepal shape.*—Ovate.
*Sepals fused or unfused.*—Unfused.
*Sepal dimensions.*—5 mm. in length and 3 mm. in width.
*Sepal margins.*—Entire.
*Sepal apex.*—Round.
*Sepal base.*—Cuneate.
*Flower fragrance.*—None observed.

Reproductive organs:
*Stamens.*—4 in number.
*Stamen shape.*—Filament.
*Stamen color.*—157A.
*Stamen dimensions.*—Two are 6 mm. in length and 0.50 mm. in width, and two are 4 mm. in length and 0.50 mm. in width.
*Anther dimensions.*—1.50 mm. in length and 0.50 mm. in width.
*Anther shape.*—Oval.
*Anther color.*—162A.
*Quantity of pollen.*—Copious but typical of the species.
*Color of pollen.*—162A.
*Pistil.*—One in number.
*Pistil color.*—138A.
*Pistil dimensions.*—6 mm. in length and 1mm. in width.
*Pistil shape.*—Filament.
*Stigma dimensions.*—1 mm. in length and 1 mm. in width.
*Stigma color.*—138A.
*Stigma shape.*—Round.
*Ovary position.*—Superior.
*Ovary color.*—138A.
*Ovary shape.*—Oval.
*Ovary dimensions.*—3 mm. in length and 1.5 mm. in width.

Seed: Seed is produced and has been observed when in the presence of other plants of the species.
*Capsule.*—Color 200A. Shape and dimentions: ovate; 6 mm in length; 2.5 mm in width.
*Seed.*—Color: 199B. Shape and dimensions: spherical; 0.60 mm–0.75 mm in diameter. Surface: Glabrous. Quantity: 30–40 seeds per capsule.

What is claimed is:

1. A new and distinct cultivar of *Jamesbrittenia* plant named 'YASAL' as described and illustrated.

* * * * *